United States Patent [19]

Omura et al.

[11] 4,353,986
[45] Oct. 12, 1982

[54] PROCESS FOR PRODUCING ANTIBIOTIC NANAOMYCIN E

[75] Inventors: Satoshi Omura, Tokyo; Haruo Tanaka, Machida; Itaru Takahashi, Kumamoto; Shinzo Ishii; Kazuyuki Mineura, both of Nagaizumi; Kunikatsu Shirahata, Machida; Masaji Kasai, Fujisawa, all of Japan

[73] Assignees: Kyowa Hakko Kogyo Kabushiki Kaisha; Kitasato Kenkyusho, both of Tokyo, Japan

[21] Appl. No.: 276,432

[22] Filed: Jun. 22, 1981

Related U.S. Application Data

[60] Division of Ser. No. 97,001, Nov. 23, 1979, Pat. No. 4,296,040, which is a continuation of Ser. No. 17,314, Mar. 5, 1979, abandoned.

[30] Foreign Application Priority Data

Mar. 7, 1978 [JP] Japan ................................ 53-25041

[51] Int. Cl.³ ....................... C12P 17/18; C12P 17/06; C12R 1/465
[52] U.S. Cl. ................................... 435/119; 435/125; 435/886
[58] Field of Search ....................... 435/124, 125, 119

[56] References Cited

U.S. PATENT DOCUMENTS

| | | | |
|---|---|---|---|
| 4,194,064 | 3/1980 | Omura et al. | 435/125 |
| 4,196,266 | 4/1980 | Omura et al. | 435/125 |
| 4,296,040 | 10/1981 | Omura et al. | 260/345.2 |

Primary Examiner—Lionel M. Shapiro
Attorney, Agent, or Firm—Wolder, Gross & Yavner

[57] ABSTRACT

The present invention teaches a new antibiotic nanaomycin E represented by the formula:

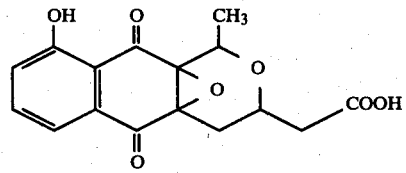

Nanaomycin E is active against Gram-positive bacteria, Trichophyton and Mycoplasma and may be used as antibacterial and therapeutic agents for humans and animals. Nanaomycin E is also a useful starting material for the preparation of nanaomycin A which latter nanaomycin has the highest activity among the various nanaomycin-type compounds. Nanaomycin E is produced by fermentation of a microorganism belonging to the genus Streptomyces and capable of producing nanaomycin E, especially *Streptomyces rosa variant notoensis* (FERM-P 2209; ATCC 31135) and recovering the same from the fermented liquor.

4 Claims, 3 Drawing Figures

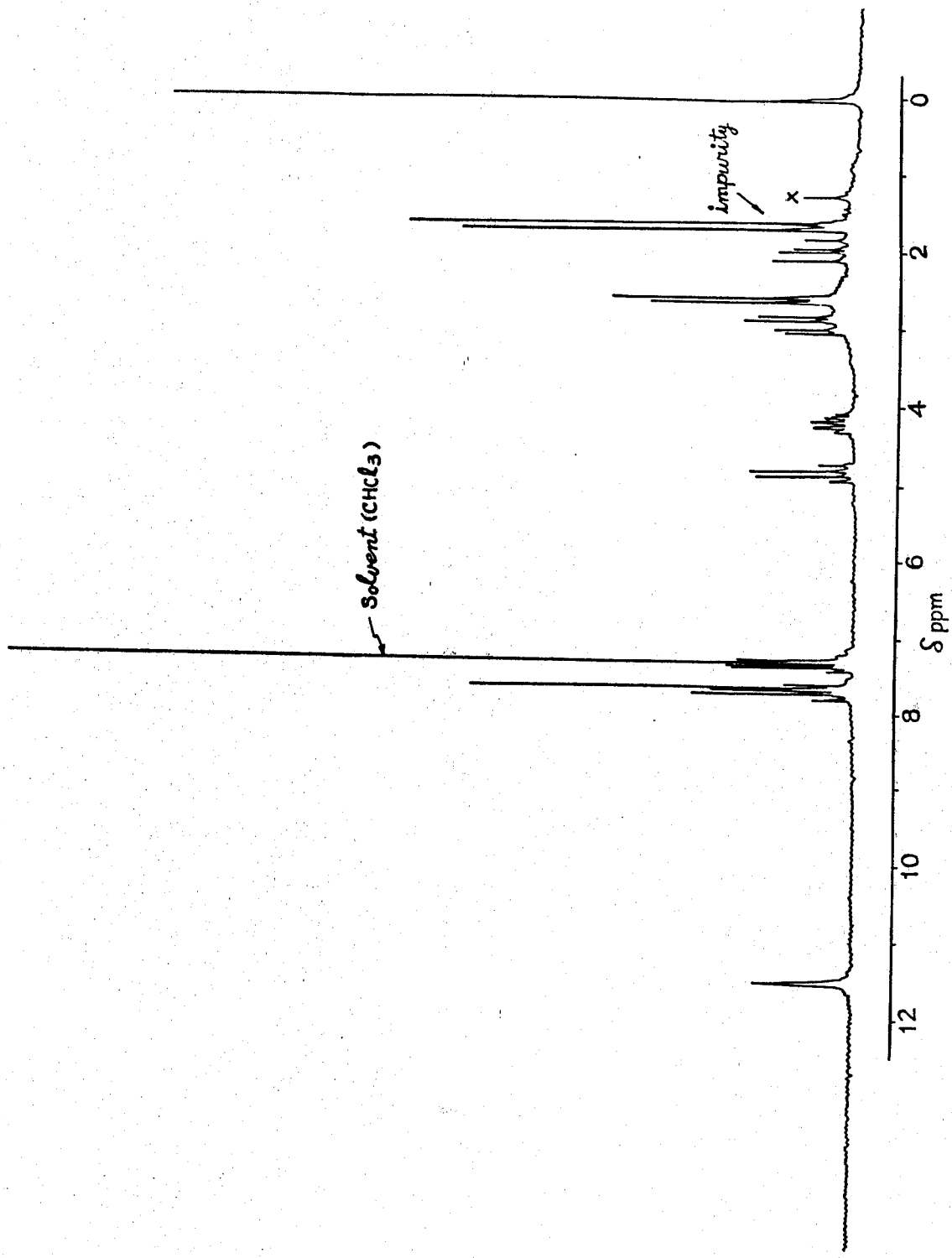

PROCESS FOR PRODUCING ANTIBIOTIC NANAOMYCIN E

This is a division, of Application Ser. No. 97,001 filed Nov. 23, 1979, now U.S. Pat. No. 4,296,040 issued Oct. 20, 1981, which is a Continuation of Ser. No. 17,314 filed Mar. 5, 1979, abandoned.

BACKGROUND OF THE INVENTION

The present invention relates to a new antibiotic designated as nanaomycin E and a process for producing the same.

Nanaomycin A is a known compound having antibiotic activity against Gram-positive bacteria, Trichophyton and Mycoplasma and may be used, for example, as antibacterial and therapeutic agents for humans and animals. Conventionally, nanaomycin A is produced by culturing a microorganism belonging to the genus Streptomyces and capable of producing nanaomycin A in a medium under aerobic conditions to accumulate nanaomycin A in the fermented liquor and nanaomycin A is recovered therefrom. A preferred strain for this purpose is Streptomyces *rosa variant notoensis* (FERM P-2209; ATCC 31135). The cultural and taxonomic characteristics of this strain are described, for example, in Japanese Patent Publication 24595/76; J. Antibiotics, 27, 363–365 (1974); ibidem, 28, 860–867 (1975); and ibidem, 28, 868–875 (1975). It is also known that by fermentation of this strain, nanaomycin B [Japanese Patent Publication 26514/76; J. Antibiotics, 27, 363–365 (1974); ibidem, 28, 868–875 (1975)], nanaomycin C [Japanese Patent Application as laid open to public inspection as Kokai Koho 133,986/77; J. Antibiotics, 28, 925–930 (1975)] and nanaomycin D [Japanese Patent Application 76589/76; J. Chemical Society, Chemical Communications, 9, 320–321 (1976)] may also be accumulated in the fermented liquor and may be recovered therefrom.

As shown by the following, nanaomycin B, C and D are structurally related to nanaomycin A and also exhibit antibiotic activities. Among them, nanaomycin A is believed to be the most useful for practical purpose because of its favorable activity, toxicity and stability. In this specification, nanaomycin A to E having the following formulas are referred to as nanaomycin-type compounds.

SUMMARY OF THE INVENTION

The present invention is based upon the discovery that a large amount of another substance having interesting properties is accumulated in the fermented liquor of said strain. This substance designated as nanaomycin E has also possesses antibiotic activity. Moreover, nanaomycin E may also serve as a starting material for the preparation of nanaomycin A.

According to the present invention, there is provided a new antibiotic, nanaomycin E, represented by the formula:

BRIEF DESCRIPTION OF THE DRAWINGS

FIGS. 1, 2 and 3 show respectively an ultraviolet absorption spectrum, infrared absorption spectrum and N.M.R. spectrum of nanaomycin E according to the present invention.

The physical, chemical and biological characteristics of nanaomycin E, in substantially pure form, are as follows:

1. Structural formula: As shown above. It was determined with reference to the following characteristics of nanaomycin E and to the structural formulas and characteristics of other nanaomycin-type compounds.

2. Appearance: Orange pillar crystals when recrystalized from n-hexane/methylene chloride.

3. Elementary analysis:

|  | C | H | N |
|---|---|---|---|
|  | 60.14% | 4.34% | 0% |
| Calculated as $C_{16}H_{14}O_7$: | 60.38% | 4.43% | 0% |

4. Molecular weight: 318. Mass spectrum [M+ (m/e)] indicates a molecular ion of 318.0760 and the theoretical value for $C_{16}H_{14}O_7$ is 318.0739.

5. Melting point: 172°–174° C.

6. Specific rotation:
$[\alpha]_D^{20} = +89.0$ (c=0.95 in methanol)

(1) nanaomycin A (2) nanaomycin B (3) nanaomycin C (4) nanaomycin D

Figure 1:
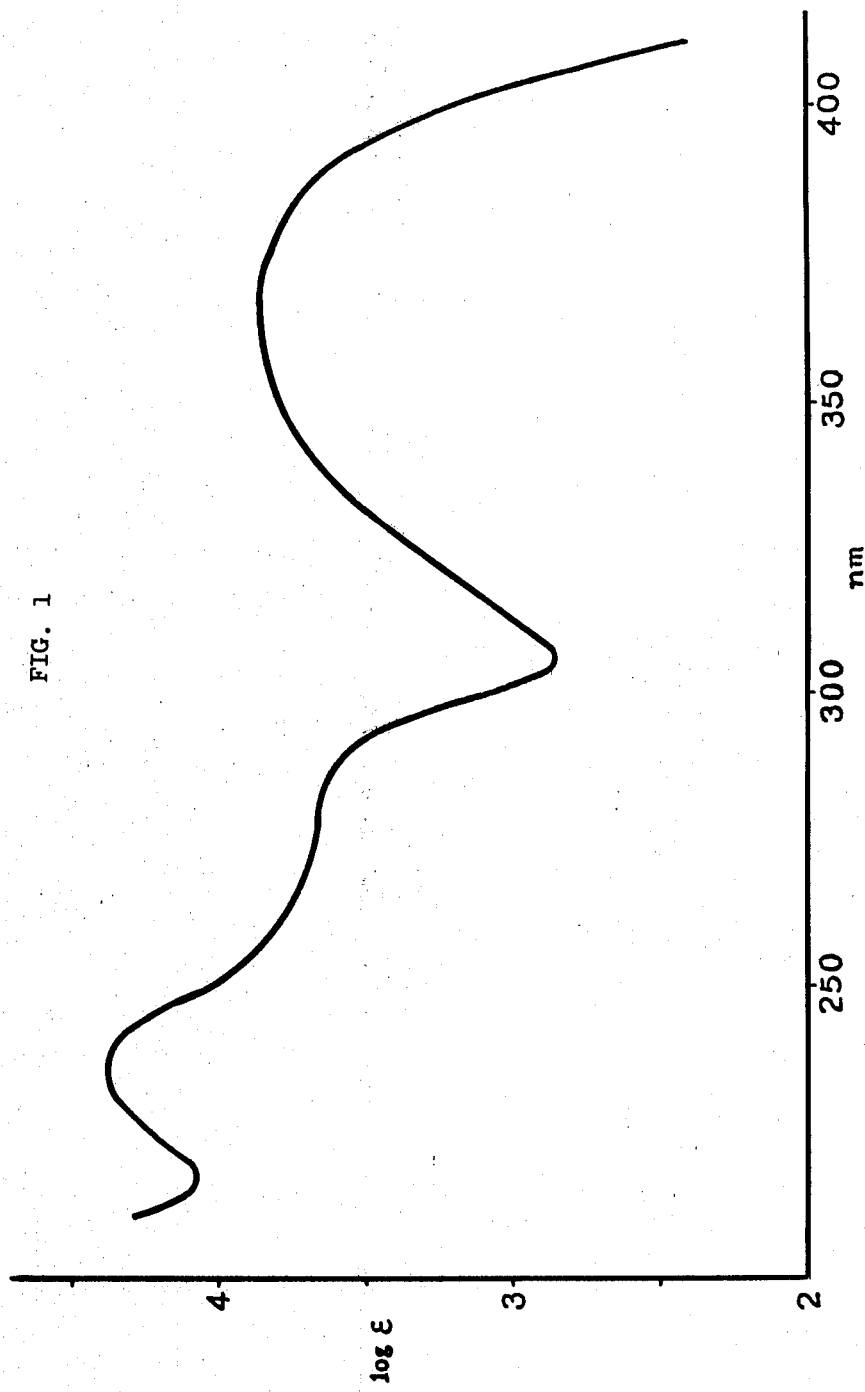

7. Ultraviolet absorption spectrum: as shown in FIG. 1

| Absorption maximum(nm) | 232 | 276 | 361 | (in methanol) |
|---|---|---|---|---|
| Molecular extinction coefficient($\epsilon$) | 15000 | 2930 | 3870 | |

Figure 2:
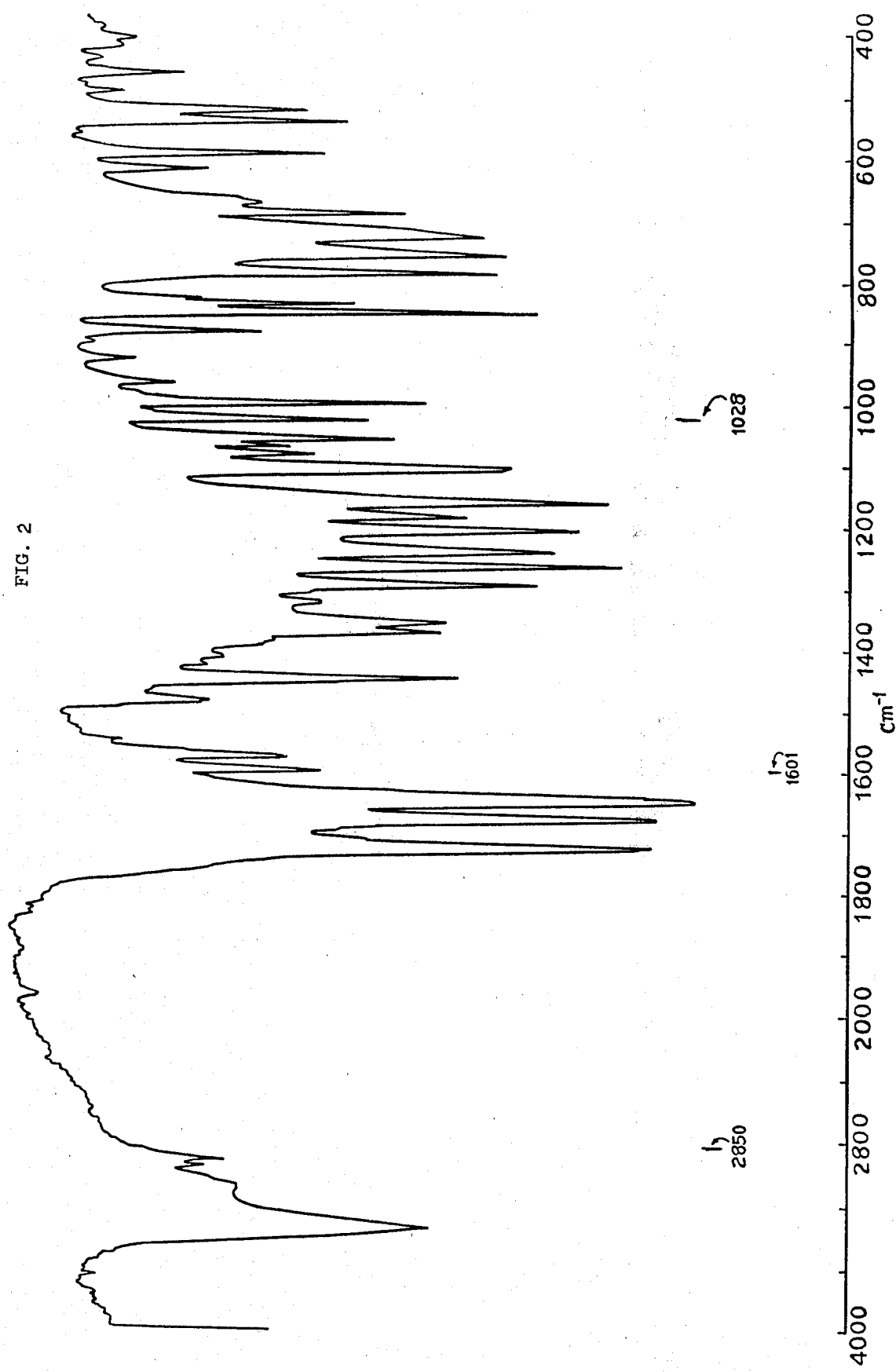

8. Infrared absorption spectrum: as shown in FIG. 2 (KBr method)

Specific, relatively strong absorption at 1270, 1650 and 1690 cm$^{-1}$

9. Solubility: Easily soluble in methanol, ethanol, ethyl acetate, butyl acetate etc. Insoluble in n-hexane, petroleum ether etc.

10. Color reaction: Positive in the reaction with ferric chloride. Negative in ninhydrin reaction and Erlich reaction.

11. Rf value: 0.45 when subjected to silica gel thin layer chromatography (TLC) using silica gel No. 5721 (commercial product of E. Merck AG., West Germany) and developed by a solvent system of chloroform/methanol (5:1 by volume).

12. N.M.R. spectrum: as shown in FIG. 3 (in CDCl$_3$)

13. Nanaomycin E also exhibits a strong yellowish fluorescence.

The antibacterial and antifungal spectrum of nanaomycin E is shown in Table 1, in which the minimum inhibitory concentration (MIC) is determined by the agar dilution method. In the case of bacteria, the determination was made after culturing at 37° C. for 20 hours by using a nutrient agar having a pH of 7.0 and, in the cases of fungi, the determination was made after culturing at 27° C. for 70 hours by using a potato-agar having a pH of 6.4.

TABLE 1

| Test organisms | MIC($\mu$g/ml) |
|---|---|
| Staphylococcus aureus FDA 209P | 25 |
| Staphylococcus aureus FS 1277 (penicillin-resistant) | 25 |
| Staphylococcus aureus KB 64 (erythromycin- and tetracycline-resistant) | 25 |
| Bacillus subtilis PCI 219 | 12.5 |
| Bacillus cereus T | 12.5 |
| Sarcina lutea PCI 1001 | 25 |
| Mycobacterium smegmatis ATCC 607 | >100 |
| Proteus vulgaris IFO 3167 | 25 |
| Nocardia asteroides | >100 |
| Escherichia coli NIHJ | 50 |
| Salmonella typhimurium | >100 |
| Shigella sonnei E 33 | >100 |
| Pseudomonas aeruginosa P 3 | >100 |
| Candida albicans | >100 |
| Saccharomyces sake | >100 |
| Piricularia oryzae | 100 |
| Aspergillus niger ATCC 6275 | >100 |
| Microsporum gypseum | 100 |
| Trichophyton interdigitale | 50 |
| Trichophyton rubrum | 50 |
| Trichophyton mentagrophytes | 50 |
| Trichophyton schoenleini | 50 |

This table indicates that the activity of nanaomycin E against Gram-positive bacteria and fungi is approximately equal to or somewhat weaker than the activities of nanaomycin A and D. LD$_{50}$ values of nanaomycin A, D and E are 46, 1.5 and 60 mg/kg respectively, when interaveneously administered to mice. Thus, nanaomycin E is of interest as an antibacterial and therapeutic agent for humans and animals.

Furthermore, some of the co-inventors of the present invention have discovered that nanaomycin E may be used as a starting material for the preparation of nanaomycin A, as is disclosed in Ser. No. 17,313 filed concurrently herewith, based upon Japanese Patent Application 25042/78 filed on 7th March 1978. This discovery is of particularly interest because, among nanaomycin-type compounds, nanaomycin A exhibits the strongest activity against Gram-positive bacteria, Trichophyton and Mycoplasma and is thus believed to be the most useful for practical purposes. Moreover, the amount of nanaomycin A accumulated in the fermented liquor is relatively small in comparison with the relatively large amount of nanaomycin E accumulated when *Streptomyces rosa* variant *notoensis* (FERM P-2209; ATCC 31135) is cultured in a medium to produce various nanaomycin-type compounds at the same time. In such cases, the amounts of nanaomycin-type compounds accumulated in the fermented liquor may vary, depending upon various culturing conditions. However, nanaomycin E constitutes the major part of the nanaomycin-type compounds accumulated in the fermented liquor and the corresponding amounts of other nanaomycins are very small. For example, in some cases, it has been observed that the fermented liquor contains 50-200 $\mu$g/ml of nanaomycin E and a relatively small amount of nanaomycin A (e.g. 7-12 $\mu$g/ml). Because nanaomycin E may be converted into nanaomycin A in high yield (for example, 60-80%), nanaomycin E is of interest as a starting material for the preparation of nanaomycin A on an industrial scale.

Nanaomycin E may be produced by culturing aerobically a microorganism belonging to the genus Streptomyces capable of producing nanaomycin E in a medium to accumulate nanaomycin E in the cultured broth and recovering the same from the cultured broth. The fermentation method for microorganisms belonging to the genus Streptomyces is well known in the art. A preferred microorganism for use in the process of the present invention is *Streptomyces rosa* variant *notoensis* (FERM P-2209; ATCC 31135) which has also been used for the production of various nanaomycin-type compounds as hereinbefore defined, although it may be possible to use any mutant thereof. The method of culturing this microorganism is well known in the art and is described in the various prior art literatures referred to hereinbefore.

The fermentation may, for example, be carried out in the following manner. Any synthetic or organic medium may be used providing it contains suitable amounts of a carbon source, a nitrogen source, an inorganic nutrient and, if desired, various other nutrients. Useful carbon sources are exemplified by various carbohydrates such as glucose, glycerol, fructose, maltose, ribose, dextrine, strach and its hydrolyzate liquor. These sources may be used alone or in combination. The concentration of carbon source is usually 5-50 g/l on the basis of the medium when calculated as glucose. It is also possible to use various organic acids such as, for example, gluconic acid, pyruvic acid, lactic acid, acetic acid; and various amino acids, for example, glycine, glutamic acid and alanine.

Nitrogen sources which may be employed in the process of the present invention are exemplified by ammonia, ammonium chloride, ammonium phosphate, ammonium sulfate, ammonium nitrate, ammonium acetate and various other inorganic and organic ammonium salts; various nitrogen-containing organic substances, for example, urea, peptone, NZ-amine, meat extract, dried yeast, yeast extract, corn steep liquor, casein hydrolyzate, fish meal and digested products thereof; and various amino acids, for example, glycine, glutamic acid and alanine.

Inorganic nutrients which may be employed in the process of the present invention are exemplified by various phosphates, magnesium sulfate, calcium carbonate and a trace amount of heavy metal salts. In the case of using a mutant strain having a nutritional requirement, it is necessary to add such required substance to the medium.

The fermentation is aerobically carried out with shaking and/or submerged conditions at a temperature of 15°–40° C. for 1–8 days for example at 20°–40° C. for 1–2 days whereby nanaomycin E is formed and accumulated in the fermented liquor. The pH of the medium is adjusted to 4–10.

As described above after completion of the fermentation, other nanaomycin-type compounds as hereinbefore defined may also be accumulated in the fermented liquor when *Streptomyces rosa variant notoensis* is cultured. In such a case, the major part of the nanaomycin-type compounds accumulated in the fermented liquor is nanaomycin E and its recovery and isolation may be effected, for example, in the following manner.

For example, the fermented liquor is extracted with a suitable solvent such as ethyl acetate under acidic conditions. The extract is concentrated to dryness under reduced pressure to give crude powders containing nanaomycin E in association with other nanaomycin-type compounds. The crude powders are subjected to silica gel column chromatography using a solvent system of benzene/ethyl acetate. The eluted fractions contain various nanaomycin-type compounds, and those containing nanaomycin E are collected and combined. The combined fractions containing nanaomycin E are concentrated under reduced pressure to obtain crude powders of nanaomycin E which are then subjected to further silica gel column chromatography carried out in a similar manner to the first column chromatography and so on, resulting in yellow-white powders of nanaomycin E. These powders are dissolved in a suitable solvent (e.g. n-hexane/methylene chloride) and concentrated to dryness under reduced pressure to obtain orange pillar crystals of nanaomycin E.

The existence of nanaomycin E described in the following examples and reference was determined by silica gel thin layer chromatography (TLC) using silica gel No. 5721 (commercially available from E. Merck AG., West Germany). The Rf value of nanaomycin E using such a system was determined as 0.45. On the other hand, a similar procedure gave Rf values of nanaomycin A and B of 0.5 and 0.3 respectively.

The following non-limitative examples illustrate the process for producing nanaomycin E according to the present invention.

EXAMPLE 1

One platinum loop of *Streptomyces rosa variant notoensis* (FERM P-2209; ATCC 31135) was taken from a slant culture and inoculated into the first seed medium (50 ml) which was placed in a 250 ml Erlenmeyer flask for culturing at a temperature of 27° C. for 2 days. The first seed culture thus-obtained was transferred to the second seed medium (500 ml) put in a 2 liter Erlenmeyer flask having a baffle for culturing at a temperature of 27° C. for a day. Both the first and second seed mediums containing glycerol (20 g/l), soybean meal (20 g/l) and sodium chloride (3 g/l) were adjusted to a pH of 7.0 before use and sterilized at a temperature of 120° C. for 20 minutes. The second seeds were collected from three flasks and combined (1.5 liter in total). The combined seeds were transferred to a main medium (18 liter) put in a 30 liter jar fermentor made of stainless steel for culturing at a temperature of 36° C. for 2 days. The fermentation was effected with aeration (20 l/min) and shaking (350 r.p.m.). The main medium contained glucose (20 g/l), meat extract (10 g/l), sodium chloride (5 g/l) and calcium carbonate (3 g/l), and adjusted to a pH of 5.0 before use. After completion of the fermentation, conc. sulfuric acid was added to the fermented liquor to give an adjusted pH of 2. Ethyl acetate (10 liter) was added to the fermented liquor which was stirred for 30 minutes to effect the extraction. After this, a filter aid (Radiolite No. 600, commercially available from Showa Kagaku Kogyo K.K., Japan) in an amount of about 3 kg was added to the liquor and the microbial bodies were removed by filtration. The ethyl acetate layer was taken from the filtrate and washed twice with water, the pH of which had been adjusted to 2 by the addition of sulfuric acid. After this, the solution was concentrated under reduced pressure up to about 10 ml. This concentrated solution was transferred to a column packed with silica gel (200 g; E. Merck) and developed by using a solvent system of benzene/ethyl acetate (10:1 by volume). The eluant was divided into fractions (each 20 ml). Nanaomycin E was determined by TLC. Nanaomycin A was found in Fraction Nos. 42–54 and nanaomycin E was found in Fraction Nos. 45 et seq. Fraction Nos. 55 et seq. contained nanaomycin E only. Fraction Nos. 1–105 did not contain nanaomycin B. Fraction Nos. 51–105 were collected and combined and the combined fractions were concentrated to dryness. The dried substance was dissolved in ethyl acetate (5 ml) and the solution was subjected to silica gel column chromatography using the same solvent system as above. Fractions of the eluate containing nanaomycin E were collected and combined, followed by concentration. When the concentrated solution was added to petroleum ether, a yellow-white powder of nanaomycin E (about 300 mg) precipitated. This powder was dissolved in a solvent of n-hexane/methylene chloride (1:2 by volume; 200 ml) and concentrated under reduced pressure to give crystals which were dried to yield orange pillar crystals of nanaomycin E (250 mg) having a purity of 99%.

EXAMPLE 2

The same strain used in Example 1 was used for this example. The first and second seed mediums contained glucose (20 g/l), soy bean meal (20 g/l) and sodium chloride (3 g/l) and the pH was adjusted to 7.0 before sterilization. The strain (one platinum loop) was inoculated into a seed medium (50 ml) and put in a 250 ml Erlenmeyer flask for culturing at a temperature of 27° C. for 2 days with shaking. The fermentation using the second seed medium was carried out in an analogous manner to that described in Example 1 to prepare the second broths which were then collected from three flasks and combined (1.5 liter in total). The combined broths were transferred to a main medium (18 liter) put in a 30 liter jar fermentor for culturing at a temperature of 36° C. for 2 days with aeration and shaking. The main medium contained glucose (10 g/l), glycerol (10 g/l), meat extract (10 g/l), sodium chloride (5 g/l) and calcium carbonate (3 g/l) and its pH was adjusted to 5.0 before sterilization. After completion of the fermentation, an analogous treatment to that described in Example 1 was carried out to isolate and purify nanaomycin E, resulting in orange pillar crystals of nanaomycin E (260 mg) having a purity of 99%.

Reference:

An aqueous solution of nanaomycin E (200 μg/ml) prepared in Example 1 was adjusted to a pH of 10 with addition of caustic soda. A reducing agent was added to the solution at a concentration of 3% by weight/volume, and the solution was kept at a temperature of 50° C. The change of the concentration of nanaomycin A formed in the solution was determined with the lapse of time. The production yield was determined at the end of the reaction. The results are shown in Table 1.

TABLE 1

| R | Reducing agent added |
| C | Concentration(μg/ml) in the aqueous solution at the end of the reaction |
| E | Nanaomycin E |
| A | Nanaomycin A |
| P.Y. | Production yield (%) |

| | | C | | |
|---|---|---|---|---|
| No. | R | E | A | P.Y. |
| 1 | Sodium thiosulfate + glucose | 0 | 140 | 73.8 |
| 2 | Sodium thiosulfate + ribose | 0 | 150 | 79.0 |
| 3 | Sodium thiosulfate + galactose | 0 | 160 | 84.2 |
| 4 | Sodium thiosulfate + xylose | 0 | 140 | 73.8 |
| 5 | Sodium thiosulfate + mannose | 0 | 130 | 68.4 |
| 6 | Sodium sulfide | 0 | 135 | 71.1 |
| 7 | Sodium sulfide + glucose | 0 | 140 | 73.8 |
| 8 | Hydrogen sulfide | 0 | 140 | 73.8 |
| 9 | Hydrogen sulfide + glucose | 0 | 145 | 76.4 |
| 10 | Sodium dithionite | 0 | 155 | 81.6 |
| 11 | Sodium dithionite + glucose | 0 | 160 | 84.2 |
| — | Without reducing agent | 200 | 0 | 0 |

What is claimed is:

1. A process for producing a compound represented by the formula:

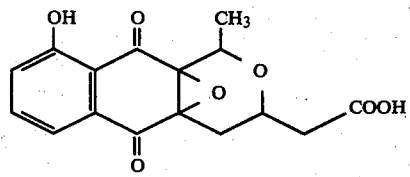

which comprises culturing the microorganism *Streptomyces rosa* variant *notoensis* in a medium under aerobic conditions to accumulate said compound in the fermented liquor and recovering same from the fermented liquor.

2. A process for producing Nanaomycin E which comprises culturing *Streptomyces rosa* variant *notoensis* in a medium under aerobic conditions at a temperature of 15° to 40° C. and a pH of 4 to 10 for a sufficient time to accumulate a substantial amount of nanaomycin E in the medium, and isolating nanaomycin E therefrom.

3. The process of claim 1, in which the microorganism is *Streptomyces rosa* variant *notoensis* (FERM P-2209; ATCC 31135).

4. The process of claim 1, in which the culturing is effected at a temperature of 15°–40° C. and a pH of 4–10 for a sufficient time to accumulate a substantial amount of nanaomycin E.